(12) United States Patent
Garcia et al.

(10) Patent No.: US 6,864,383 B2
(45) Date of Patent: Mar. 8, 2005

(54) OPHTHALMIC COMPOSITIONS FOR TREATING OCULAR HYPERTENSION

(75) Inventors: Maria L. Garcia, Edison, NJ (US); Gregory J. Kaczorowski, Edison, NJ (US); Ying-Duo Gao, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 48 days.

(21) Appl. No.: 10/466,878

(22) PCT Filed: Jan. 25, 2002

(86) PCT No.: PCT/US02/03049

§ 371 (c)(1), (2), (4) Date: Jul. 16, 2003

(87) PCT Pub. No.: WO02/060863

PCT Pub. Date: Aug. 8, 2002

(65) Prior Publication Data

US 2004/0054213 A1 Mar. 18, 2004

Related U.S. Application Data

(60) Provisional application No. 60/264,954, filed on Jan. 30, 2001.

(51) Int. Cl.$^7$ .................. C07C 327/08; A61K 31/21
(52) U.S. Cl. .................. 558/254; 558/256; 564/154; 514/513; 514/516
(58) Field of Search .................. 558/254; 564/154; 514/513, 616

(56) References Cited

U.S. PATENT DOCUMENTS 5,994,293 A * 11/1999 Baxter et al. .................. 514/2
6,239,305 B1 * 5/2001 Suzuki et al. ............... 558/254

* cited by examiner

Primary Examiner—Shailendra Kumar
(74) Attorney, Agent, or Firm—Sylvia A. Ayler; Valerie J. Camara

(57) ABSTRACT

This invention relates to the use of potent potassium channel blockers or a formulation thereof in the treatment of glaucoma and other conditions which leads to elevated intraocular pressure in the eye of a patient. This invention also relates to the use of such compounds to provide a neuroprotective effect to the eye of mammalian species, particularly humans.

32 Claims, No Drawings

OPHTHALMIC COMPOSITIONS FOR TREATING OCULAR HYPERTENSION

This application is a 371 of PCT/US02/03049, filed Jan. 25, 2002 Which claims benefit from U.S. Provisional Application No. 60/264,954, filed Jan. 30, 2001.

BACKGROUND OF THE INVENTION

Glaucoma is a degenerative disease of the eye wherein the intraocular pressure is too high to permit normal eye function. As a result, damage may occur to the optic nerve head and result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by the majority of ophthalmologists to represent merely the earliest phase in the onset of glaucoma.

Many of the drugs formerly used to treat glaucoma proved unsatisfactory. The early methods of treating glaucoma employed pilocarpine and produced undesirable local effects that made this drug, though valuable, unsatisfactory as a first line drug. More recently, clinicians have noted that many β-adrenergic antagonists are effective in reducing intraocular pressure. While many of these agents are effective for this purpose, there exist some patients with whom this treatment is not effective or not sufficiently effective. Many of these agents also have other characteristics, e.g., membrane stabilizing activity, that become more apparent with increased doses and render them unacceptable for chronic ocular use and can also cause cardiovascular effects.

Although pilocarpine and β-adrenergic antagonists reduce intraocular pressure, none of these drugs manifests its action by inhibiting the enzyme carbonic anhydrase, and thus they do not take advantage of reducing the contribution to aqueous humor formation made by the carbonic anhydrase pathway.

Agents referred to as carbonic anhydrase inhibitors decrease the formation of aqueous humor by inhibiting the enzyme carbonic anhydrase. While such carbonic anhydrase inhibitors are now used to treat intraocular pressure by systemic and topical routes, current therapies using these agents, particularly those using systemic routes are still not without undesirable effects. Because carbonic anhydrase inhibitors have a profound effect in altering basic physiological processes, the avoidance of a systemic route of administation serves to diminish, if not entirely eliminate, those side effects caused by inhibition of carbonic anhydrase such as metabolic acidosis, vomiting, numbness, tingling, general malaise and the like. Topically effective carbonic anhydrase inhibitors are disclosed in U.S. Pat. Nos. 4,386,098; 4,416,890; 4,426,388; 4,668,697; 4,863,922; 4,797,413; 5,378,703, 5,240,923 and 5,153,192.

Prostaglandins and prostaglandin derivatives are also known to lower intraocular pressure. U.S. Pat. No. 4,883,819 to Bito descibes the use and synthesis of PGAs, PGBs and PGCs in reducing intraocular pressure. U.S. Pat. No. 4,824,857 to Goh et al. describes the use and synthesis of PGD2 and derivatives thereof in lowering intraocular pressure including derivatives wherein C-10 is replaced with nitrogen. U.S. Pat. No. 5,001,153 to Ueno et al. describes the use and synthesis of 13,14-dihydro-15-keto prostaglandins and prostaglandin derivatives to lower intraocular pressure. U.S. Pat. No. 4,599,353 describes the use of eicosanoids and eicosanoid derivatives including prostaglandins and prostaglandin inhibitors in lowering intraocular pressure.

Prostaglandin and prostaglandin derivatives lower intraocular pressure by increasing uveoscleral outflow. This is true for both the F type and A type of Pgs and hence presumably also for the B, C, D, E and J types of prostaglandins and derivatives thereof. A problem with using prostaglandin derivatives to lower intraocular pressure is that these compounds often induce an initial increase in intraocular pressure, can change the color of eye pigmentation and cause proliferation of some tissues surrounding the eye.

As can be seen, there are several current therapies for treating glaucoma and elevated intraocular pressure, but the efficacy and the side effect profiles of these agents are not ideal. Recently potassium channel blockers were found to reduce intraocular pressure in the eye and therefore provide yet one more approach to the treatment of ocular hypertension and the degenerative ocular conditions related thereto. Blockage of potassium channels can diminish fluid secretion, and under some circumstances, increase smooth muscle contraction and would be expected to lower IOP and have neuroprotective effects in the eye. (see U.S. Pat. Nos. 5,573,758 and 5,925,342; Moore, et al., Invest. Ophthalmol. Vis. Sci 38, 1997; WO 89/10757, WO94/28900, and WO 96/33719).

SUMMARY OF THE INVENTION

This invention relates to potent potassium channel blockers, their use or a formulation thereof in the treatment of glaucoma and other conditions which are related to elevated intraocular pressure in the eye of a patient. This invention also relates to the use of such compounds to provide a neuroprotective effect to the eye of mammalian species, particularly humans. More particularly this invention relates to the treatment of glaucoma and/or ocular hypertension (elevated intraocular pressure) using ethanecarbothioic S acid ester compounds having the structural formula I:

FORMULA I

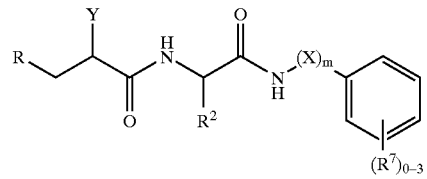

or a pharmaceutically acceptable salt, enantiomer, diastereomer or mixture thereof:

wherein,

R and $R^2$ independently represent $C_{1-6}$ alkyl, $(CH_2)_n$aryl, $(CH_2)_n$heteroaryl, $(CH_2)_n$heterocycloalkyl, said alkyl, aryl or heteroaryl optionally substituted with 1–3 groups of $R^3$;

Y represents —$(CH_2)_n SCOR^4$;

X represents $CH_2$, or O (in which m does not exist);

$R^3$ represents hydrogen, $C_{1-6}$ alkoxy, $C_{1-6}$ alkyl, $CF_3$, nitro, amino, cyano, $C_{1-6}$ alkylamino, or halogen and $R^4$ represents $C_{1-6}$ alkoxy, or $C_{1-6}$ alkyl;

$R^7$ represents H, halo, OH, $NO_2$, $NH_2$, CN, alkoxy, —COO—, alkoxycarbonyl, haloalkyl, alkoxycarbonylalkyl, or alkylsulphonyl;

m represents 1–3; and/or n represents 0–3.

This and other aspects of the invention will be realized upon inspection of the invention as a whole.

DETAILED DESCRIPTION OF THE INVENTION

The present invention is directed to a method for decreasing elevated intraocular pressure or treating glaucoma by administration, preferably topical or intra-camaral administration, of a composition containing a potassium channel blocker of Formula I and a pharmaceutically acceptable carrier.

One embodiment of this invention is realized when R is $C_{1-6}$ alkyl, or $(CH_2)_n$ aryl, and all other variables are as originally described.

Another embodiment of this invention is realized when $R_2$ is $C_{1-6}$ alkyl, or $(CH_2)_n$ aryl, and all other variables are as originally described.

Yet another embodiment of this invention is realized when X is $CH_2$ and all other variables are as originally described.

Still another embodiment of this invention is realized when Y is —$(CH_2)_n SCOR^4$ wherein n=0, and all other variables are as originally described.

Another embodiment of this invention is realized when Y is —$(CH_2)_n SCOR^4$, wherein n=1–3, and all other variables are as originally described.

A preferred embodiment of this invention is realized when R is $(CH_2)_n$ aryl, $R^2$ is $C_{1-6}$ alkyl, Y is $(CH_2)_n SCOR^4$, X is $CH_2$ and m=1.

Another preferred embodiment of this invention is realized when R is $(CH_2)_n$aryl, $R^2$ is $C_{1-6}$ alkyl, Y is $(CH_2)_n SCOR^4$, X is $CH_2$ and m=2.

Still another preferred embodiment of this invention is realized when R is $C_{1-6}$ alkyl, $R^2$ is $(CH_2)_n$aryl, Y is $(CH_2)_n SCOR^4$, X is $CH_2$ and m=2.

Yet another preferred embodiment of this invention is realized when R is $(CH_2)_n$aryl, $R^2$ is $(CH_2)_n$aryl, Y is $(CH_2)_n SCOR^4$, X is $CH_2$ and m=2.

Yet another preferred embodiment of this invention is realized when $R^7$ is H and all other variables are as originally described.

Preferred compounds of this invention are:

Compound 1

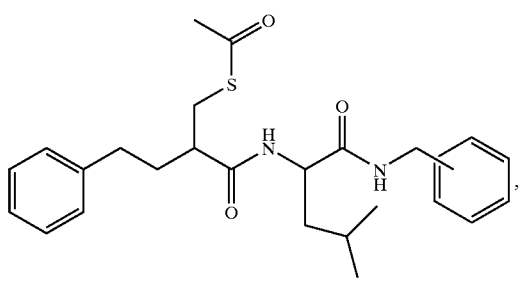

Compound 2

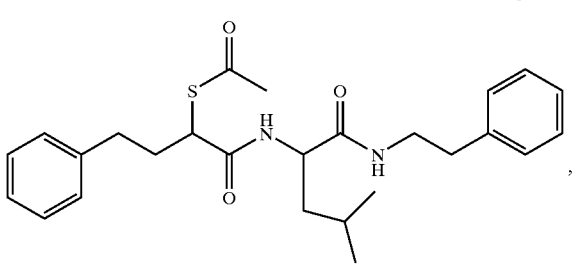

Compound 3

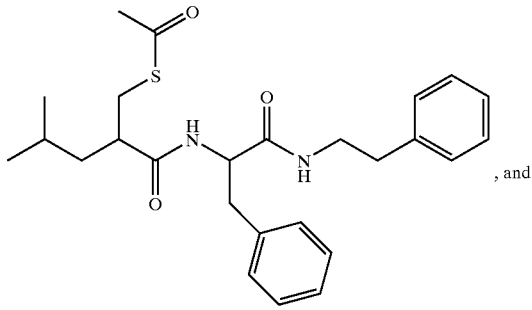

, and

Compound 4

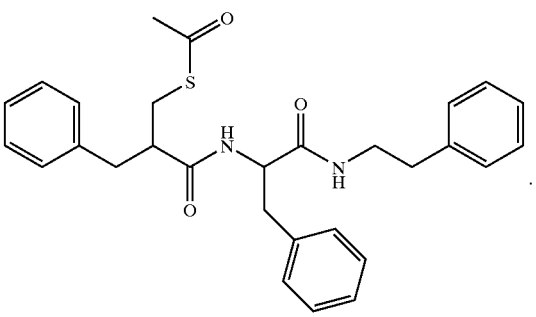

The invention is described herein in detail using the terms defined below unless otherwise specified.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

Alkoxy refers to $C_1$–$C_6$ alkyl-O—, with the alkyl group optionally substituted as described herein.

Halogen (halo) refers to chlorine, fluorine, iodine or bromine.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

The term "heterocycloalkyl" refers to a cycloalkyl group (nonaromatic) in which one of the carbon atoms in the ring is replaced by a heteroatom selected from O, S or N, and in which up to three additional carbon atoms may be replaced by hetero atoms.

The term "heteroatom" means O, S or N, selected on an independent basis.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole.

This invention is also concerned with a method of treating ocular hypertension or glaucoma by administering to a patient in need thereof one of the compounds of formula I in combination with a β-adrenergic blocking agent such as timolol, a parasympathomimetic agent such as pilocarpine, carbonic anhydrase inhibitor such as dorzolamide, acetazolamide, metazolamide or brinzolamide, a prostaglandin such as latanoprost, rescula, S1033 or a hypotensive lipid derived from PGF2α prostaglandins such as prostamide (AGN 192024). An example of a hypotensive lipid (the carboxylic acid group on the α-chain link of the basic prostaglandin structure is replaced with electrochemically neutral substituents) is that in which the carboxylic acid group is replaced with a $C_{1-6}$ alkoxy group such as $OCH_3$ ($PGF_{2a}$ 1-$OCH_3$), or a hydroxy group ($PGF_{2a}$ 1-OH).

Preferred potassium channel blockers are calcium activated potassium channel blockers. More preferred potassium channel blockers are high conductance, calcium activated potassium (Maxi-K) channel blockers. Maxi-K channels are a family of ion channels that are prevalent in neuronal, endocrine smooth muscle and epithelial tissues and which are gated by membrane potential and intracellular $Ca^{2+}$.

Intraocular pressure (IOP) is controlled by aqueous humor dynamics. Aqueous humor is produced at the level of the non-pigmented ciliary epithelium and is cleared primarily via outflow through the trabecular meshwork. Aqueous humor inflow is controlled by ion transport processes. It is thought that maxi-K channels in non-pigmented ciliary epithelial cells indirectly control chloride secretion by two mechanisms; these channels maintain a hyperpolarized membrane potential (interior negative) which provides a driving force for chloride efflux from the cell, and they also provide a counter ion ($K^+$) for chloride ion movement. Water moves passively with KCl allowing production of aqueous humor. Inhibition of maxi-K channels in this tissue would diminish inflow. Maxi-K channels have also been shown to control the contractility of certain smooth muscle tissues, and, in some cases, channel blockers can contract quiescent muscle, or increase the myogenic activity of spontaneously active tissue. Contraction of ciliary muscle would open the trabecular meshwork and stimulate aqueous humor outflow, as occurs with pilocarpine. Therefore maxi-K channels could profoundly influence aqueous humor dynamics in several ways; blocking this channel would decrease IOP by affecting inflow or outflow processes or by a combination of affecting both inflow/outflow processes.

The present invention is based upon the finding that maxi-K channels, if blocked, inhibit aqueous humor production by inhibiting net solute and $H_2O$ efflux and therefore lower IOP. This finding suggests that maxi-K channel blockers are useful for treating other ophthamological dysfunctions such as macular edema and macular degeneration. It is known that lowering IOP promotes blood flow to the retina and optic nerve. Accordingly, the compounds of this invention are useful for treating macular edema and/or macular degeneration.

Macular edema is swelling within the retina within the critically important central visual zone at the posterior pole of the eye. An accumulation of fluid within the retina tends to detach the neural elements from one another and from their local blood supply, creating a dormancy of visual function in the area.

Glaucoma is characterized by progressive atrophy of the optic nerve and is frequently associated with elevated intraocular pressure (IOP). It is possible to treat glaucoma, however, without necessarily affecting IOP by using drugs that impart a neuroprotective effect. See Arch. Ophthalmol. Vol. 112, January 1994, pp. 37–44; Investigative Ophthamol. & Visual Science, 32, 5, April 1991, pp. 1593–99. It is believed that maxi-K channel blockers which lower IOP are useful for providing a neuroprotective effect. They are also believed to be effective for increasing retinal and optic nerve head blood velocity and increasing retinal and optic nerve oxygen by lowering IOP, which when coupled together benefits optic nerve health. As a result, this invention further relates to a method for increasing retinal and optic nerve head blood velocity, increasing retinal and optic nerve oxygen tension as well as providing a neuroprotective effect or a combination thereof.

As indicated above, potassium channel antagonists are useful for a number of physiological disorders in mammals, including humans. Ion channels, including potassium channels, are found in all mammalian cells and are involved in the modulation of various physiological processes and normal cellular homeostasis. Potassium ions generally control the resting membrane potential, and the efflux of potassium ions causes repolarization of the plasma membrane after cell depolarization. Potassium channel antagonists prevent repolarization and enable the cell to stay in the depolarized, excited state.

There are a number of different potassium channel subtypes. Physiologically, one of the most important potassium channel subtypes is the Maxi-K channel which is present in neuronal and endocrine tissue, smooth muscle and epithelial tissue. Intracellular calcium concentration ($Ca^{2+}_i$) and membrane potential gate these channels. For example, Maxi-K channels are opened to enable efflux of potassium ions by an increase in the intracellular $Ca^{2+}$ concentration or by membrane depolarization (change in potential). Elevation of intracellular calcium concentration is required for neurotransmitter release. Modulation of Maxi-K channel activity therefore affects transmitter release from the nerve terminal by controlling membrane potential, which in turn affects the influx of extracellular $Ca^{2+}$ through voltage-gated calcium channels. The compounds of the present invention are therefore useful in the treatment of neurological disorders in which neurotransmitter release is impaired.

A number of marketed drugs function as potassium channel antagonists. The most important of these include the compounds Glyburide, Glipizide and Tolbutamide. These potassium channel antagonists are useful as antidiabetic agents. The compounds of this invention may be combined with one or more of these compounds to treat diabetes.

Potassium channel antagonists are also utilized as Class 3 anti-arrhythmic agents and to treat acute infarctions in humans. A number of naturally occuring toxins are known to block potassium channels including Apamin, Iberiotoxin, Charybdotoxin, Noxiustoxin, Kaliotoxin, Dendrotoxin(s), mast cell degranuating (MCD) peptide, and β-Bungarotoxin (β-BTX). The compounds of this invention may be combined with one or more of these compounds to treat arrhythmias.

Depression is related to a decrease in neurotransmitter release. Current treatments of depression include blockers of neurotransmitter uptake, and inhibitors of enzymes involved in neurotransmitter degradation which act to prolong the lifetime of neurotransmitters.

Alzheimer's disease is also characterized by a diminished neuro-transmitter release. Alzheimer's disease is a neurodegenerative disease of the brain leading to severely impaired cognition and functionality. This disease leads to progressive regression of memory and learned functions. Alzheimer's disease is a complex disease that affects cholinergic neurons, as well as serotonergic, noradrenergic and other central neurotransmitter systems. Manifestations of Alzheimer's disease extend beyond memory loss and include personality changes, neuromuscular changes, seizures, and occasionally psychotic features.

Alzheimer's disease is the most common type of dementia in the United States. Some estimates suggest that up to 47% of those older than 85 years have Alzheimer's disease. Since the average age of the population is on the increase, the frequency of Alzheimer's disease is increasing and requires urgent attention. Alzheimer's is a difficult medical problem because there are presently no adequate methods available for its prevention or treatment.

Three classes of drugs are being investigated for the treatment of Alzheimer's disease. The first class consists of compounds that augment acetyl-choline neurotransmitter function. Currently, cholinergic potentiators such as the anticholinesterase drugs are being used in the treatment of Alzheimer's disease. In particular, physostigmine (eserine), an inhibitor of acetylcholinesterase, has been used in its treatment. The administration of physostigmine has the drawback of being considerably limited by its short half-life of effect, poor oral bioavailability, and severe dose-limiting side-effects, particularly towards the digestive system. Tacrine (tetrahydroaminocridine) is another cholinesterase inhibitor that has been employed; however, this compound may cause hepatotoxicity.

A second class of drugs that are being investigated for the treatment of Alzheimer's disease is nootropics that affect neuron metabolism with little effect elsewhere. These drugs improve nerve cell function by increasing neuron metabolic activity. Piracetam is a nootropic that may be useful in combination with acetyl-choline precursors and may benefit Alzheimer's patients who retain some quantity of functional acetylcholine release in neurons. Oxiracetam is another related drug that has been investigated for Alzheimer treatment.

A third class of drugs is those drugs that affect brain vasculature. A mixture of ergoloid mesylates is used for the treatment of dementia. Ergoloid mesylates decrease vascular resistance and thereby increase cerebral blood flow. Also employed are calcium channel blocking drugs including Nimodipine which is a selective calcium channel blocker that affects primarily brain vasculature.

Other miscellaneous drugs are targeted to modify other defects found in Alzheimer's disease. Selegiline, a monoamine oxidase B inhibitor which increases brain dopamine and norepinephrine has reportedly caused mild improvement in some Alzheimer's patients. Aluminum chelating agents have been of interest to those who believe Alzheimer's disease is due to aluminum toxicity. Drugs that affect behavior, includeing neuroleptics, and anxiolytics have been employed. Side effects of neuroleptics range from drowsiness and anti cholinergic effects to extrapyramidal side effects; other side effects of these drugs include seizures, inappropriate secretion of antidiuretic hormone, jaundice, weight gain and increased confusion. Anxiolytics, which are mild tranquilizers, are less effective than neuroleptics, but also have milder side effects. Use of these behavior-affecting drugs, however, remains controversial. The present invention is related to novel compounds which are useful as potassium channel antagonists. It is believed that certain diseases such as depression, memory disorders and Alzheimers disease are the result of an impairment in neurotransmitter release. The potassium channel antagonists of the present invention may therefore be utilized as cell excitants which should stimulate an unspecific release of neurotransmitters such as acetylcholine, serotonin and dopamine. Enhanced neurotransmitter release should reverse the symptoms associated with depression and Alzheimers disease.

The compounds within the scope of the present invention exhibit potassium channel antagonist activity and thus are useful in disorders associated with potassium channel malfunction. A number of cognitive disorders such as Alzheimer's Disease, memory loss or depression may benefit from enhanced release of neuro-transmitters such as serotonin, dopamine or acetylcholine and the like. Blockage of Maxi-K channels maintains cellular depolarization and therefore enhances secretion of these vital neurotransmitters.

The compounds of this invention may be combined with anticholin-esterase drugs such as physostigmine (eserine) and Tacrine (tetrahydroaminocridine), nootropics such as Piracetam, Oxiracetam, ergoloid mesylates, selective calcium channel blockers such as Nimodipine, or monoamine oxidase B inhibitors such as Selegiline, in the treatment of Alzheimer's disease. The compounds of this invention may also be combined with Apamin, Iberiotoxin, Charybdotoxin, Noxiustoxin, Kaliotoxin, Dendrotoxin(s), mast cell degranuating (MCD) peptide, β-Bungarotoxin (β-BTX) or a combination thereof in treating arrythmias. The compounds of this invention may further be combined with Glyburide, Glipizide, Tolbutamide or a combination thereof to treat diabetes.

The herein examples illustrate but do not limit the claimed invention. Each of the claimed compounds are potassium channel antagonists and are thus useful in the described neurological disorders in which it is desirable to maintain the cell in a depolarized state to achieve maximal neurotransmitter release. The compounds produced in the present invention are readily combined with suitable and known pharmaceutically acceptable excipients to produce compositions which may be administered to mammals, including humans, to achieve effective potassium channel blockage.

The maxi-K channel blockers used in the instant invention can be administered in a therapeutically effective amount intravaneously, subcutaneously, topically, transdermally, parenterally or any other method known to those skilled in the art. Ophthalmic pharmaceutical compositions are preferably adapted for topical administration to the eye in the form of solutions, suspensions, ointments, creams or as a solid insert. Ophthalmic formulations of this compound may contain from 0.01 to 5% and especially 0.5 to 2% of medicament. Higher dosages as, for example, about 10% or lower dosages can be employed provided the dose is effective in reducing intraocular pressure, treating glaucoma, increasing blood flow velocity or oxygen tension. For a single dose, from between 0.001 to 5.0 mg, preferably 0.005 to 2.0 mg, and especially 0.005 to 1.0 mg of the compound can be applied to the human eye.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, peanut oil, polyalkylene glycols, petroleum based jelly, ethyl cellulose, ethyl oleate, carboxymethyl-cellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a microparticle formulation. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyactylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, gellan gum, and mixtures of said polymer.

Suitable subjects for the administration of the formulation of the present invention include primates, man and other animals, particularly man and domesticated animals such as cats and dogs.

The pharmaceutical preparation may contain non-toxic auxiliary substances such as antibacterial components which are non-injurious in use, for example, thimerosal, benzalkonium chloride, methyl and propyl paraben, benzyldodecinium bromide, benzyl alcohol, or phenylethanol; buffering ingredients such as sodium chloride, sodium borate, sodium acetate, sodium citrate, or gluconate buffers; and other conventional ingredients such as sorbitan monolaurate, triethanolamine, polyoxyethylene sorbitan monopalmitylate, ethylenediamine tetraacetic acid, and the like.

The ophthalmic solution or suspension may be administered as often as necessary to maintain an acceptable IOP level in the eye. It is contemplated that administration to the mammalian eye will be about once or twice daily.

For topical ocular administration the novel formulations of this invention may take the form of solutions, gels, ointments, suspensions or solid inserts, formulated so that a unit dosage comprises a therapeutically effective amount of the active component or some multiple thereof in the case of a combination therapy.

Methodologies for making the compounds of this invention can be gleaned from WO 9512603, WO9635712, EP 322633, JO 3002-117 and U.S. Pat. No. 3,246,025. In particular, the compounds of this invention can be made, with some modification, in accordance with U.S. Pat. No. 5,629,343 and WO 9616027, which are incorporated herein by reference. The following examples, given by way of illustration, is demonstrative of the present invention.

EXAMPLE 1

Diethyl2-[2-(phenyl)ethyl]malonate

According to the described procedure (J. Med. Chem., 1984, 27, 967–978), to a 2 liter 3-neck round bottom flask was attached a pressure equalized addition funnel and a water cooled reflux condenser. A large Teflon coated magnetic stirring bar was added and the flask flamed dried under nitrogen. Sodium hydroxide (60% in mineral oil, 42 g, 1.06 moles) was added to the flask and the mineral oil removed by washing the solid three times with 40 mL of hexane. One liter of dry tetrahydrofuran (THF) (distilled over potassium/benzophenone) was added to the flask under nitrogen. A mineral oil bubbler was attached by a rubber septum to the flask and diethyl malonate was added dropwise over 1 h, keeping the temperature <18° C. When hydrogen evolution had ceased, 107.5 grams of 1-bromoethyl benzene (1.06 mole) was added dropwise over 30 minutes with cooling (<30°). The solution was gently refluxed overnight. The mixture was cooled to room temperature and poured into 200 mL of ice water containing 150 mmole of HCl and stirred 5 minutes. The organic layer was separated and the aqueous layer extracted with 3×100 mL of ether. The organic layers were combined and washed with 2×100 mL of saturated sodium bicarbonate and 1×100 mL of brine. The solution was dried over anhydrous MgSO4. The ether was removed under reduced pressure and the product distilled under vacuum (bp=146–148 @ 1.5 mm Hg). Recovered 203 g of product (yield=72%).

Monoethyl 2-[2-(phenyl)ethyl]malonate acid

Following the reported procedure (J. Med. Chem, 1982, 24, 109–113), diethyl 2-[2-(phenyl)ethyl-malonate (200 g, 0.756 mole) was dissolved in 600 mL of absolute ethanol in a 2 liter round bottom flask fitted with a Teflon coated stirring bar. The solution was cooled to 5° C., in an ice bath. Then 49.9 g of potassium hydroxide (85%) in 600 mL of absolute ethanol was added dropwise to the rapidly stirring solution over a 2 hour period with the solution temperature kept under 15° C. The solution was stirred under nitrogen overnight at 25° C. Ethanol was removed under reduced pressure and the syrupy residue dissolved in 800 mL of ice water. The solution was washed with 2×200 ml of ether, the aqueous layer acidified with concentrated HCl (pH<3) and extracted 3×300 mL of ether. The combined ether layer was washed with brine and dried over anhydrous MgSO4. The solution was filtered and the ether removed under reduced pressure to give a clear oil. Recovered 162 g of product (90% yield).

2-Methylene-4-phenylbutyric acid, ethyl ester

Monoethyl 2-[2-(phenyl)ethyl]malonic acid (47.2 g, 200 mole) was added to 40 mL round bottom flask fitted with a Teflon coated stirring bar. Piperidine (3 mL) and paraformaldehyde (8.4 g, 280 mmole) were added to the flask and the flask was heated to 55–60° C., until gas evolution ceased. TLC indicated that no starting material remained. The solution was worked up by removing the solvent under reduced pressure. Water (50 mL) and enough 12N HCl was added to the flask to acidify the mixture (pH>3). The mixture was extracted with ether (3×50 mL) and back extracted with brine. The solution was dried over $MgSO_4$ and filtered. The reaction mixture was shown to be clean by NMR and TLC and used without further purification. Recovered 36.3 g material (89% yield).

2-Methylene-4-phenylbutyric acid 4-phenyl-2-methylenebutyric acid, ethyl ester (10 g, 49 mmole) was dissolved in 100 mL of absolute ethanol, Potassium hydroxide (3.32 g, 85%, 50 mmole) was added to the solution and the solution stirred overnight at room temperature. After 18 hours, all of the ester was hydolyzed. The solvent was removed under reduced pressure and the syrup dissolved in water. Enough concentrated HCl was added to acidify the solution (pH>3) and the product was extracted with ether (3×50 mL). The solution was dried over $MgSO_4$, filtered and the solvent removed under reduced pressure. Recovered 8.6 g of product (97% yield).

2-[Acetylthiomethyl]-4-phenylbutyric acid

A 250 mL round bottomed flask, fitted with a Teflon magnetic stirring bar and a reflux condenser, was filled with 150 mL of toluene, 0.5 mL piperidine and 8.6 g (49 mmole) of 4-phenyl-2-methylenebutyric acid. Then 4.1 g (54 mmole) of thiolacetic acid was added to the solution and the mixture heated to reflux for 8 hours under nitrogen. $^1$H-NMR analysis of the reaction mixture indicated some starting material remained. Another 1 g of thiolacetic acid was added and the mixture stirred at reflux for an additional 4 hours. By $^1$H-NMR, all of the starting material was seen to have reacted. The solution was cooled to 5° C., and 100 mL of ether added to the mixture. The excess thiolacetic acid was removed by extraction (3×50 mL 2% sodium bicarbonate). Then 50 mL of 1N HCl was added to the organic layer and the solution shaken vigorously. The organic layer was separated and dried over $MgSO_4$. The solution was filtered and the solvent removed under reduced pressure. Recovered 10.0 g of product (81% yield).

N-(2-Acetylthiomethyl-4-phenylbutanoyl)-(L)-Leucine t-butyl ester

To a solution of 4-phenyl-2-[acetylthio-methyl]butyric acid (3.57 g, 14.2 mmole) in 66 mL of THF at 0° C., was added (S)-leucine, t-butyl ester (2.91 g 15.6 mmole) and 1-hydroxybenzotriazole hydrate (HOBT$H_2$O, 2.86 g, 21.2 mmole) and N-methylmorpholine (4.29 g, 42.4 mmole). The mixture was stirred at 0° C. for 15 minutes, then 5.42 g of 1-ethyl-3-(3-dimethyl-aminopropyl) carbodiimide hydrochloride (EDC'HCl, 28.3 mmol) was added and the mixture stirred overnight. The solution was worked up by adding 100 mL methylene chloride and the mixture extracted with 3×50 mL of 5% sodium bicarbonate and washed with 2×50 mL of brine. The organic layer was dried over MgSO4, filtered, and the solvent removed under reduced pressure. The residue was purified by flash chromatography on silica gel eluted with methylene chloride/ethyl acetate (95/5). The product was separated as diastereomeric (R,S) and (S,S) fractions. The absolute stereochemistry of each fraction was not determined. Higher Rf material=1.78 g; lower Rf material= 1.90 g.

N-(2-Acetylthiomethyl-4-phenylbutanoyl)-(L)-leucine, N-phenylamide

To a solution of N-(2-acetylthiomethyl-4-phenylbutanoyl)-(L)-leucine (derived from the higher Rf TLC fraction) (182 mg, 0.5 mmole) in 2 mL of THF at 0° C. was added aniline (93 mg, 1.0 mmole) and 1-hydroxybenzotriazole hydrate (HOBT'$H_2$O), 101 mg, 0.75 mole) and N-methylmorpholine (202 mg, 2.0 mmole). The mixture was stirred at 0° C. for 15 minutes, then 192 mg of 1-ethyl-3-(3-dimethyl-aminopropyl)carbodiimide hydrochloride (EDC.HCl, 1.0 mmole) was added and the mixture stirred overnight. The solution was worked up by adding 7 mL methylene chloride and the mixture extracted with 3×3 ml of 5% sodium bicarbonate, then 2×2 mL of brine. The organic layer was dried over MgSO4, filtered and the solvent removed under reduced pressure. The residue was purified by flash column chromatography on silica gel eluted with methylene chloride/ethyl acetate (90/10) to obtain 110 mg of product (yield=50%).

Functional Assays

A. Maxi-K Channel—TsA-201 Cells

The identification of inhibitors of the Maxi-K channel can be accomplished using Aurora Biosciences technology, and is based on the ability of expressed Maxi-K channels to set cellular resting potential after transient transfection of both α and β1 subunits of the channel in TsA-201 cells. In the absence of inhibitors, cells display a hyperpolarized membrane potential, negative inside, close to $E_K$ (−80 mV) which is a consequence of the activity of the Maxi-K channel. Blockade of the Maxi-K channel will cause cell depolarization. Changes in membrane potential can be determined with voltage-sensitive fluorescence resonance energy transfer (FRET) dye pairs that use two components, a donor coumarin ($CC_2$DMPE) and an acceptor oxanol (DiSBAC$_2$(3)). Oxanol is a lipophilic anion and distributes across the membrane according to membrane potential. Under normal conditions, when the inside of the cell is negative with respect to the outside, oxanol is accumulated at the outer leaflet of the membrane and excitation of coumarin will cause FRET to occur. Conditions that lead to membrane depolarization will cause the oxanol to redistribute to the inside of the cell, and, as a consequence, to a decrease in FRET. Thus, the ratio change (donor/acceptor) increases after membrane depolarization.

Transient transfection of the Maxi-K channel in TsA-201 cells can be carried out as previously described (Hanner et al. (1998) J. Biol. Chem. 273, 16289–16296) using FUGENE6™ as the transfection reagent. Twenty four hours after transfection, cells are collected in $Ca^{2+}$—$Mg^{2+}$-free Dulbecco's phosphate-buffered saline (D-PBS), subjected to centrifugation, plated onto 96-well poly-d-lysine coated plates at a density of 60,000 cells/well, and incubated overnight. The cells are then washed 1× with D-PBS, and loaded with 100 µl of 4 µM $CC_2$DMPE-0.02% pluronic-127 in D-PBS. Cells are incubated at room temperature for 30 min in the dark. Afterwards, cells are washed 2× with D-PBS and loaded with 100 µl of 6 µM DiSBAC$_2$(3) in (mM): 140 NaCl, 0.1 KCl, 2 CaCl$_2$, 1 MgCl$_2$, 20 Hepes-NaOH, pH 7.4, 10 glucose. Test compounds are diluted into this solution, and added at the same time. Cells are incubated at room temperature for 30 min in the dark.

Plates are loaded into a voltage/ion probe reader (VIPR) instrument, and the fluorescence emission of both $CC_2$DMPE and DiSBAC$_2$(3) are recorded for 10 sec. At this point, 100 µl of high-potassium solution (mM): 140 KCl, 2 CaCl$_2$, 1 MgCl$_2$, 20 Hepes-KOH, pH 7.4, 10 glucose are added and the fluorescence emission of both dyes recorded for an additional 10 sec. The ratio $CC_2DMPE/DiSBAC_2(3)$, before addition of high-potassium solution equals 1. In the absence of any inhibitor, the ratio after addition of high-potassium solution varies between 1.65–2.2. When the Maxi-K channel has been completely inhibited by either a known standard or test compound, this ratio remains at 1. It is possible, therefore, to titrate the activity of a Maxi-K channel inhibitor by monitoring the concentration-dependent change in the fluorescence ratio.

The compounds of this invention were found to cause concentration-dependent inhibition of the fluorescence ratio with $IC_{50}$'s in the range of about 10 nM to about 5 $\mu$M, more preferably from about 100 nM to about 1 $\mu$M.

B. Maxi-K Channel Assay—HEK-293 Cells

Under appropriate conditions the maxi-K channel sets the resting potential of the HEK-293 cells stably transfected with this channel. Generally, addition of high-potassium solution causes the cells to depolarize and this activity can be monitored with fluorescence dyes using a voltage/ion probe reader (VIPR) instrument. Preincubation of the cells with an inhibitor of the maxi-K channel will lead to cell depolarization. Under these conditions, addition of the high-potassium solution will not cause any change in the emission properties of the fluorescence dyes because the cells are already predepolarized. Because HEK-293 cells have endogenous potassium conductances, these conductances have to be eliminated so that the maxi-K channel is the predominate one setting the resting potential at $E_K$. Elimination is achieved when the HEK-293 cells are incubated with a potassium channel blocker prior to adding a test compound. The consequence of this pharmacological manipulation is the generation of a very large screening window where the fluorescence signal denoting a hyperpolarized resting potential is abolished by selective maxi-K channel blockers.

Preferred potassium channel blockers are those that selectively eliminate the endogenous potassium conductances of the HEK-293 cells without affecting maxi-K channel activity. Untransfected HEK-293 cells are commercially available. The HEK-293 cells can be transfected as described herein.

The identification of inhibitors of the Maxi-K channel is based on the ability of expressed Maxi-K channels to set cellular resting potential after transfection of both alpha and beta 1 subunits of the channel in HEK-293 cells and after being incubated with potassium channel blockers that selectively eliminate the endogenous potassium conductances of HEK-293 cells. In the absence of maxi-K channel inhibitors, the transfected HEK-293 cells display a hyperpolarized membrane potential, negative inside, close to $E_K$ (−80 mV) which is a consequence of the activity of the maxi-K channel. Blockade of the Maxi-K channel by incubation with maxi-K channel blockers will cause cell depolarization. Changes in membrane potential can be determined with voltage-sensitive fluorescence resonance energy transfer (FRET) dye pairs that use two components, a donor coumarin ($CC_2DMPE$) and an acceptor oxanol ($DiSBAC_2(3)$).

Oxanol is a lipophilic anion and distributes across the membrane according to membrane potential. Under normal conditions, when the inside of the cell is negative with respect to the outside, oxanol is accumulated at the outer leaflet of the membrane and excitation of coumarin will cause FRET to occur. Conditions that lead to membrane depolarization will cause the oxanol to redistribute to the inside of the cell, and, as a consequence, to a decrease in FRET. Thus, the ratio change (donor/acceptor) increases after membrane depolarization, which determines if a test compound actively blocks the maxi-K channel.

The HEK-293 cells were obtained from the American Type Culture Collection, 12301 Parklawn Drive, Rockville, Md., 20852 under accession number ATCC CRL-1573. Any restrictions relating to public access to the cell lines shall be irrevocably removed upon patent issuance.

Transfection of the alpha and beta1 subunits of the maxi-K channel in HEK-293 cells was carried out as follows: HEK-293 cells were plated in 100 mm tissue culture treated dishes at a density of $3 \times 10^6$ cells per dish, and a total of five dishes were prepared. Cells were grown in a medium consisting of Dulbecco's Modified Eagle Medium (DMEM) supplemented with 10% Fetal Bovine serum, 1× L-Glutamine, and 1× Penicillin/Streptomycin, at 37° C., 10% $CO_2$. For transfection with Maxi-K h$\alpha$ (pCIneo) and Maxi-K h$\beta$1 (pIRESpuro) DNAs, 150 $\mu$l FuGENE6™ was added dropwise into 10 ml of serum free/phenol-red free DMEM and allowed to incubate at room temperature for 5 minutes. Then, the FuGENE6™ solution was added dropwise to a DNA solution containing 25 $\mu$g of each plasmid DNA, and incubated at room temperature for 30 minutes. After the incubation period, 2 ml of the FuGENE6™/DNA solution was added dropwise to each plate of cells and the cells were allowed to grow two days under the same conditions as described above. At the end of the second day, cells were put under selection media which consisted of DMEM supplemented with both 600 $\mu$g/ml G418 and 0.75 $\mu$g/ml puromycin. Cells were grown until separate colonies were formed. Five colonies were collected and transferred to a 6 well tissue culture treated dish. A total of 75 colonies were collected. Cells were allowed to grow until a confluent monolayer was obtained. Cells were then tested for the presence of maxi-K channel alpha and beta1 subunits using an assay that monitors binding of $^{125}$I-iberiotoxin-D19Y/Y36F to the channel. Cells expressing $^{125}$I-iberiotoxin-D19Y/Y36F binding activity were then evaluated in a functional assay that monitors the capability of maxi-K channels to control the membrane potential of transfected HEK-293 cells using fluorescence resonance energy transfer (FRET) ABS technology with a VIPR instrument. The colony giving the largest signal to noise ratio was subjected to limiting dilution. For this, cells were resuspended at approximately 5 cells/ml, and 200 $\mu$l were plated in individual wells in a 96 well tissue culture treated plate, to add ca. one cell per well. A total of two 96 well plates were made. When a confluent monolayer was formed, the cells were transferred to 6 well tissue culture treated plates. A total of 62 wells were transferred. When a confluent monolayer was obtained, cells were tested using the FRET-functional assay. Transfected cells giving the best signal to noise ratio were identified and used in subsequent functional assays.

1. To measure binding of $^{125}$I-iberiotoxin-D19Y/Y36F to transfected HEK-293 cells, cells were plated in poly-D-lysine treated 96 wells at a density of 40,000 cells/well. Cells were grown overnight under selection medium. Then, the medium is removed and 200 $\mu$l of a solution containing about 70 pM $^{125}$I-iberiotoxin-D19Y/Y36F in selection medium is added per well. For determination of nonspecific binding the same medium also contained 100 nM unlabeled iberiotoxin. Cells are incubated with this solution for four hours at 37° C., 10% $CO_2$. After incubation, radioactive medium is removed and cells are washed one time with D-PBS. Then, 200 $\mu$l of Microscint-20 is added to each well and radioactivity associated with the cells is determined in a Packard Topcount instrument.

The transfected cells (2E+06 Cells/mL) are then plated on 96-well poly-D-lysine plates at a density of about 100,000 cells/well and incubated for about 16 to about 24 hours. The medium is aspirated of the cells and the cells washed one time with 100 μl of Dulbecco's phosphate buffered saline (D-PBS). One hundred microliters of about 9 μM coumarin (CC$_2$DMPE)-0.02% pluronic-127 in D-PBS per well is added and the wells are incubated in the dark for about 30 minutes. The cells are washed two times with 100 μl of Dulbecco's phosphate-buffered saline and 100 μl of about 4.5 μM of oxanol (DiSBAC$_2$(3)) in (mM) 140 NaCl, 0.1 KCl, 2 CaCl$_2$, 1 MgCl$_2$, 20 Hepes-NaOH, pH 7.4, 10 glucose is added. Three micromolar of an inhibitor of endogenous potassium conductance of HEK-293 cells such as Compounds A or B (see below) is added. A maxi-K channel blocker is added (about 3 micromolar to about 10 micromolar) and the cells are incubated at room temperature in the dark for about 30 minutes.

The plates are loaded into a voltage/ion probe reader (VIPR) instrument, and the fluorescence emission of both CC$_2$DMPE and DiSBAC$_2$(3) are recorded for 10 sec. At this point, 100 μl of high-potassium solution (mM): 140 KCl, 2 CaCl$_2$, 1 MgCl$_2$, 20 Hepes-KOH, pH 7.4, 10 glucose are added and the fluorescence emission of both dyes recorded for an additional 10 sec. The ratio CC$_2$DMPE/DiSBAC$_2$(3), before addition of high-potassium solution equals 1. In the absence of maxi-K channel inhibitor, the ratio after addition of high-potassium solution varies between 1.65–2.2. When the Maxi-K channel has been completely inhibited by either a known standard such as compounds 1–4 or test compound, this ratio remains at 1. It is possible, therefore, to titrate the activity of a Maxi-K channel inhibitor by monitoring the concentration-dependent change in the fluorescence ratio. Compounds A and B are:

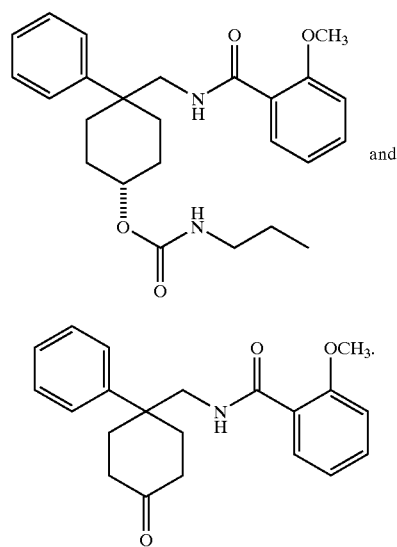

Compound A and

Compound B

C. Electrophysiological Assays of Compound Effects on High-conductance Calcium-activated Potassium Channels Human Non-pigmented Ciliary Epithelial Cells The activity of high-conductance calcium-activated potassium (maxi-K) channels in human non-pigmented ciliary epithelial cells was determined using electrophysiological methods. Currents through maxi-K channels were recorded in the inside-out configuration of the patch clamp technique, where the pipette solution faces the extracellular side of the channel and the bath solution faces the intracellular side. Excised patches contained one to about fifty maxi-K channels. Maxi-K channels were identified by their large single channel conductance (250–300 pS), and by sensitivity of channel gating to membrane potential and intracellular calcium concentration. Membrane currents were recorded using standard electrophysiological techniques. Glass pipettes (Garner 7052) were pulled in two stages with a Kopf puller (model 750), and electrode resistance was 1–3 megohms when filled with saline. Membrane currents were recorded with EPC9 (HEKA Instruments) or Axopatch ID (Axon Instruments) amplifiers, and digital conversion was done with ITC-16 interfaces (Instrutech Corp). Pipettes were filled with (mM); 150 KCl, 10 Hepes, 1 MgCl$_2$, 0.01 CaCl$_2$, 3.65 KOH, pH 7.20. The bath (intracellular) solution was identical, except, in some cases, calcium was removed, 1 mM EGTA was added and 20 mM KCl was replaced with 20 mM KF to eliminate calcium to test for calcium sensitivity of channel gating. Drugs were applied to the intracellular side of the channel by bath perfusion.

Human non-pigmented ciliary epithelial cells were grown in tissue culture as described (Martin-Vasallo, P., Ghosh, S., and Coca-Prados, M., 1989, J. Cell. Physiol. 141, 243–252), and plated onto glass cover slips prior to use. High resistance seals (>1 Gohm) were formed between the pipette and cell surface, and inside out patches were excised. Maxi-K channels in the patch were identified by their gating properties; channel open probability increased in response to membrane depolarization and elevated intracellular calcium. In patches used for pharmacological analysis, removing intracellular calcium eliminated voltage-gated currents. Maxi-K currents were measured after depolarizing voltage steps or ramps that caused channel opening.

The compounds of this invention were applied to the intracellular side of the channel in appropriate concentrations (0.001 to 10 μM). The compounds reduced channel open probability, and this effect was reversed upon washout of compounds from the experimental chamber. The IC50 for block of maxi-K channels under these conditions for the compounds of this invention ranged from about 0.5 nM to about 300 nM.

What is claimed is:

1. A compound selected from the group consisting of:

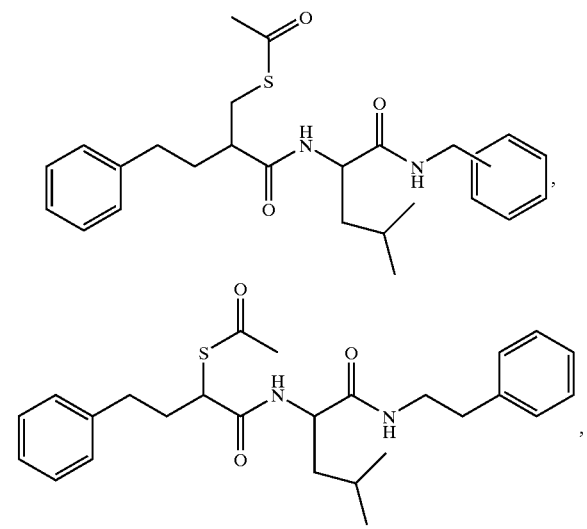

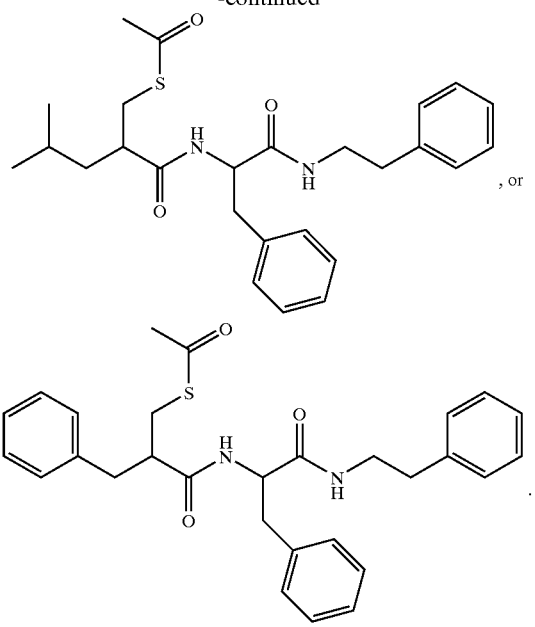
, or

2. A method for treating ocular hypertension or glaucoma comprising administration to a patient in need of such treatment a therapeutically effective amount of a compound of structural formula I:

FORMULA I

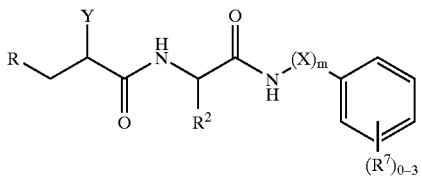

or a pharmaceutically acceptable salt, enantiomer, diastereomer or mixture thereof:
wherein,
R and $R^2$ independently represent $C_{1-6}$ alkyl, $(CH_2)_n$aryl, $(CH_2)_n$heteroaryl, $(CH_2)_n$heterocycloalkyl, said alkyl, aryl or heteroaryl optionally substituted with 1–3 groups of $R^3$;
Y represents —$(CH_2)_n SCOR^4$;
X represents $CH_2$, or O (in which m does not exist);
$R^3$ represents hydrogen, $C_{1-6}$ alkoxy, $C_{1-6}$ alkyl, $CF_3$, nitro, amino, cyano, $C_{1-6}$ alkylamino, or halogen and
$R^4$ represents $C_{1-6}$ alkoxy, or $C_{1-6}$ alkyl;
$R^7$ represents H, halo, OH, $NO_2$, $NH_2$, CN, alkoxy, —COO—, alkoxycarbonyl, haloalkyl, alkoxycarbonylalkyl, or alkylsulphonyl
m represents 1–3;
n represents 0–3.

3. The method according to claim 2 wherein the compound of formula I is applied as a topical formulation.

4. A method according to claim 2 wherein R is $C_{1-6}$ alkyl, or $(CH_2)_n$ aryl, and all other variables are as originally described.

5. A method according to claim 2 wherein $R_2$ is $C_{1-6}$ alkyl, or $(CH_2)_n$aryl, and all other variables are as originally described.

6. A method according to claim 2 wherein X is $CH_2$ and all other variables are as originally described.

7. A method according to claim 2 wherein Y is —$(CH_2)_n SCOR^4$ wherein n=0, and all other variables are as originally described.

8. A method according to claim 2 wherein Y is —$(CH_2)_n SCOR^4$, n=1–3, and all other variables are as originally described.

9. A method according to claim 2 wherein R is $(CH_2)_n$ aryl, $R^2$ is $C_{1-6}$ alkyl, Y is $(CH_2)_n SCOR^4$, X is $CH_2$ and m=1.

10. A method according to claim 2 wherein R is $(CH_2)_n$ aryl, $R^2$ is $C_{1-6}$ alkyl, Y is $(CH_2)_n SCOR^4$, X is $CH_2$ and m=2.

11. A method according to claim 2 wherein R is $C_{1-6}$ alkyl, $R^2$ is $(CH_2)_n$aryl, Y is $(CH_2)_n SCOR^4$, X is $CH_2$ and m=2.

12. A method according to claim 2 wherein R is $(CH_2)_n$ aryl, $R^2$ is $(CH_2)_n$aryl, Y is $(CH_2)_n SCOR^4$, X is $CH_2$ and m=2.

13. A method according to claim 3 wherein the topical formulation is a solution or suspension.

14. A method according to claim 3 wherein an active ingredient belonging to the group consisting of: β-adrenergic blocking agent, parasympathomimetic agent, carbonic anhydrase inhibitor, and a prostaglandin or a prostaglandin derivative is optionally added to the formulation.

15. A method according to claim 14 wherein the β-adrenergic blocking agent is timolol; the parasympathomimetic agent is pilocarpine; the carbonic anhydrase inhibitor is dorzolamide, acetazolamide, metazolamide or brinzolamide; the prostaglandin is latanoprost or rescula, and the prostaglandin derivative is a hypotensive lipid derived from PGF2α prostaglandins.

16. A method for treating macular edema or macular degeneration comprising administration to a patient in need of such treatment a pharmaceutically effective amount of a compound of structural formula I:

FORMULA I

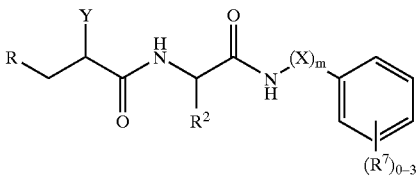

or a pharmaceutically acceptable salt, enantiomer, diastereomer or mixture thereof:
wherein,
R and $R^2$ independently represent $C_{1-6}$ alkyl, $(CH_2)_n$aryl, $(CH_2)_n$heteroaryl, $(CH_2)_n$heterocycloalkyl, said alkyl, aryl or heteroaryl optionally substituted with 1–3 groups of $R^3$;
Y represents —$(CH_2)_n SCOR^4$;
X represents $CH_2$, or O (in which m does not exist);
$R^3$ represents hydrogen, $C_{1-6}$ alkoxy, $C_{1-6}$ alkyl, $CF_3$, nitro, amino, cyano, $C_{1-6}$ alkylamino, or halogen and
$R^4$ represents $C_{1-6}$ alkoxy, or $C_{1-6}$ alkyl;
$R^7$ represents H, halo, OH, $NO_2$, $NH_2$, CN, alkoxy, —COO—, alkoxycarbonyl, haloalkyl, alkoxycarbonylalkyl, or alkylsulphonyl;
m represents 1–3; and/or
n represents 0–3.

17. The method according to claim 16 wherein the compound of formula I is applied as a topical formulation.

18. A method according to claim 16 wherein the compound is:

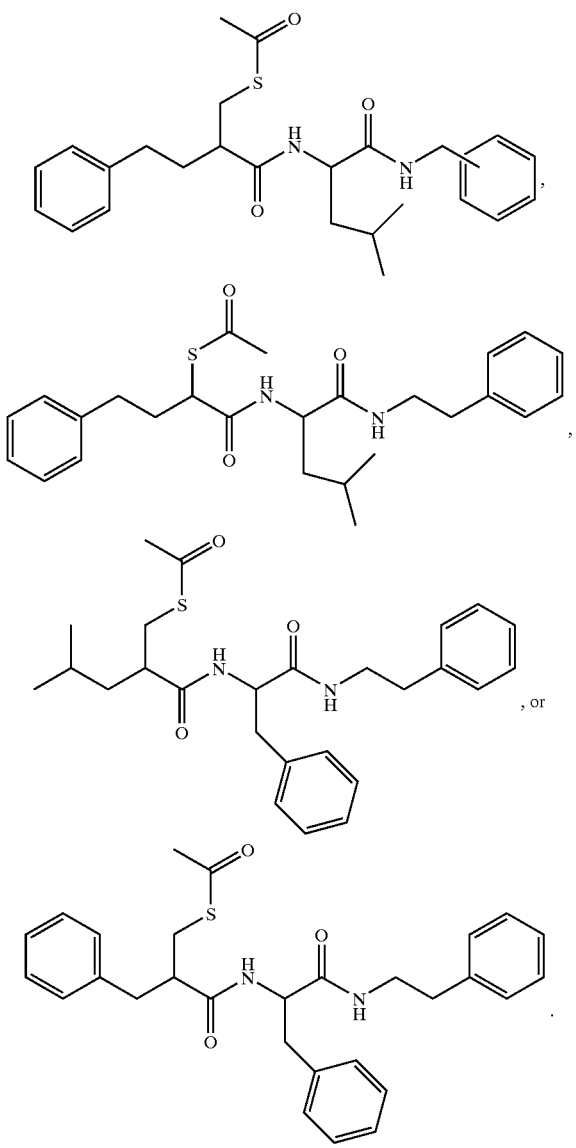

19. A method for increasing retinal and optic nerve head blood velocity or increasing retinal and optic nerve oxygen tension comprising administration to a patient in need of such treatment an effective ocular hypertensive formulation containing a potassium channel blocker of structural formula I:

FORMULA I

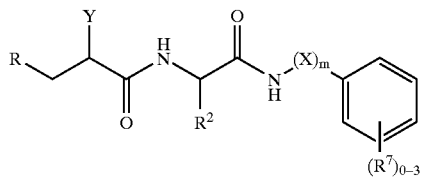

or a pharmaceutically acceptable salt, enantiomer, diastereomer or mixture thereof:
wherein, R and $R^2$ independently represent $C_{1-6}$ alkyl, $(CH_2)_n$aryl, $(CH_2)_n$heteroaryl, $(CH_2)_n$heterocycloalkyl, said alkyl, aryl or heteroaryl optionally substituted with 1–3 groups of $R^3$;

Y represents —$(CH_2)_n SCOR^4$;

X represents $CH_2$, or O (in which m does not exist);

$R^3$ represents hydrogen, $C_{1-6}$ alkoxy, $C_{1-6}$ alkyl, $CF_3$, nitro, amino, cyano, $C_{1-6}$ alkylamino, or halogen and $R^4$ represents $C_{1-6}$ alkoxy, or $C_{1-6}$ alkyl;

$R^7$ represents H, halo, OH, $NO_2$, $NH_2$, CN, alkoxy, —COO—, alkoxycarbonyl, haloalkyl, alkoxycarbonylalkyl, or alkylsulphonyl;

m represents 1–3; and/or n represents 0–3.

20. The method according to claim 19 wherein the compound of formula I is applied as a topical formulation.

21. A method according to claim 19 wherein the compound is:

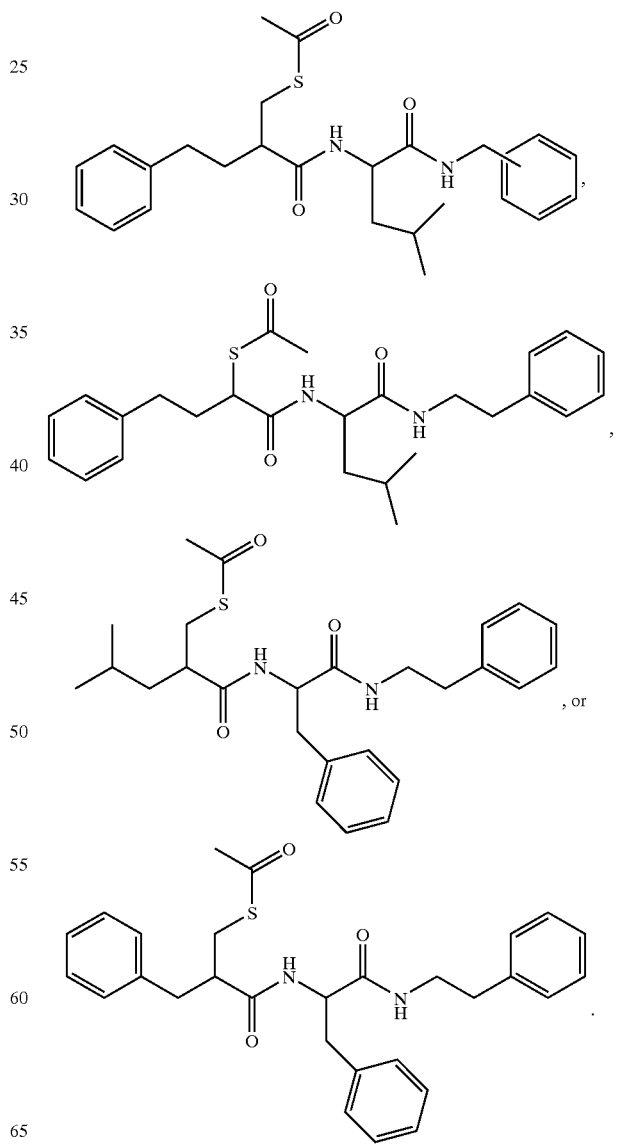

22. A method for providing a neuroprotective effect comprising administration to a patient in need of such treatment a therapeutically effective amount of structural formula I:

FORMULA I

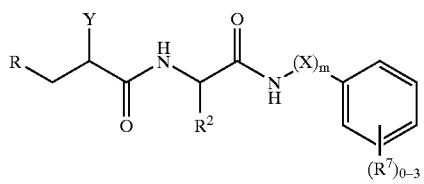

or a pharmaceutically acceptable salt, enantiomer, diastereomer or mixture thereof:

wherein,

R and $R^2$ independently represent $C_{1-6}$ alkyl, $(CH_2)_n$aryl, $(CH_2)_n$heteroaryl, $(CH_2)_n$heterocycloalkyl, said alkyl, aryl or heteroaryl optionally substituted with 1–3 groups of $R^3$;

Y represents —$(CH_2)_n SCOR^4$;

X represents $CH_2$, or O (in which m does not exist);

$R^3$ represents hydrogen, $C_{1-6}$ alkoxy, $C_{1-6}$ alkyl, $CF_3$, nitro, amino, cyano, $C_{1-6}$ alkylamino, or halogen and $R^4$ represents $C_{1-6}$ alkoxy, or $C_{1-6}$ alkyl;

$R^7$ represents H, halo, OH, $NO_2$, $NH_2$, CN, alkoxy, —COO—, alkoxycarbonyl, haloalkyl, alkoxycarbonylalkyl, or alkylsulphonyl;

m represents 1–3; and/or n represents 0–3.

23. The method according to claim 22 wherein the compound of formula I is applied as a topical formulation.

24. A method according to claim 22 wherein the compound is:

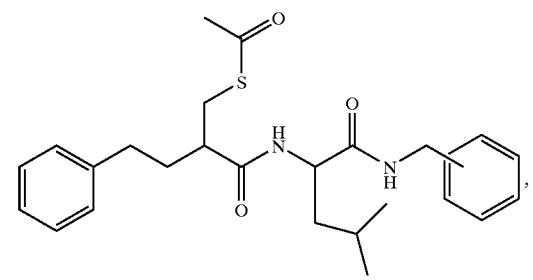

,

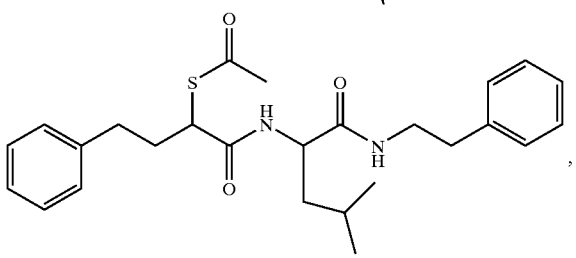

,

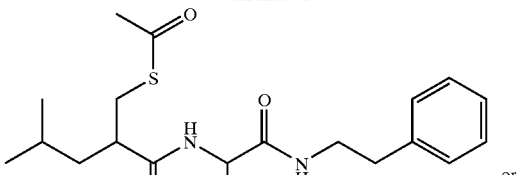

, or

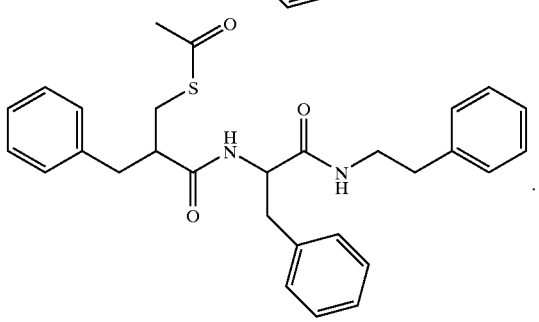

.

25. A method according to claim 2 in which the topical formulation optionally contains xanthan gum or gellan gum.

26. A method for treating ocular hypertension or glaucoma comprising administration to a patient in need of such treatment a therapeutically effective amount of structural formula I:

FORMULA I

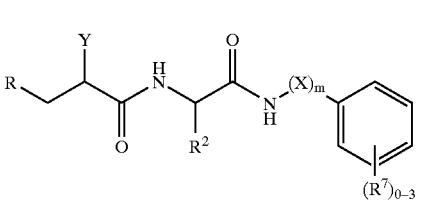

or a pharmaceutically acceptable salt, enantiomer, diastereomer or mixture thereof:

wherein,

R and $R^2$ independently represent $C_{1-6}$ alkyl, $(CH_2)_n$aryl, $(CH_2)_n$heteroaryl, $(CH_2)_n$heterocycloalkyl, said alkyl, aryl or heteroaryl optionally substituted with 1–3 groups of $R^3$;

Y represents —$(CH_2)_n SCOR^4$;

X represents $CH_2$, or O (in which m does not exist);

$R^3$ represents hydrogen, $C_{1-6}$ alkoxy, $C_{1-6}$ alkyl, $CF_3$, nitro, amino, cyano, $C_{1-6}$ alkylamino, or halogen and $R^4$ represents $C_{1-6}$ alkoxy, or $C_{1-6}$ alkyl;

$R^7$ represents H, halo, OH, $NO_2$, $NH_2$, CN, alkoxy, —COO—, alkoxycarbonyl, haloalkyl, alkoxycarbonylalkyl, or alkylsulphonyl;

m represents 1–3; and/or n represents 0–3.

27. A method according to claim 26 wherein the compound is:

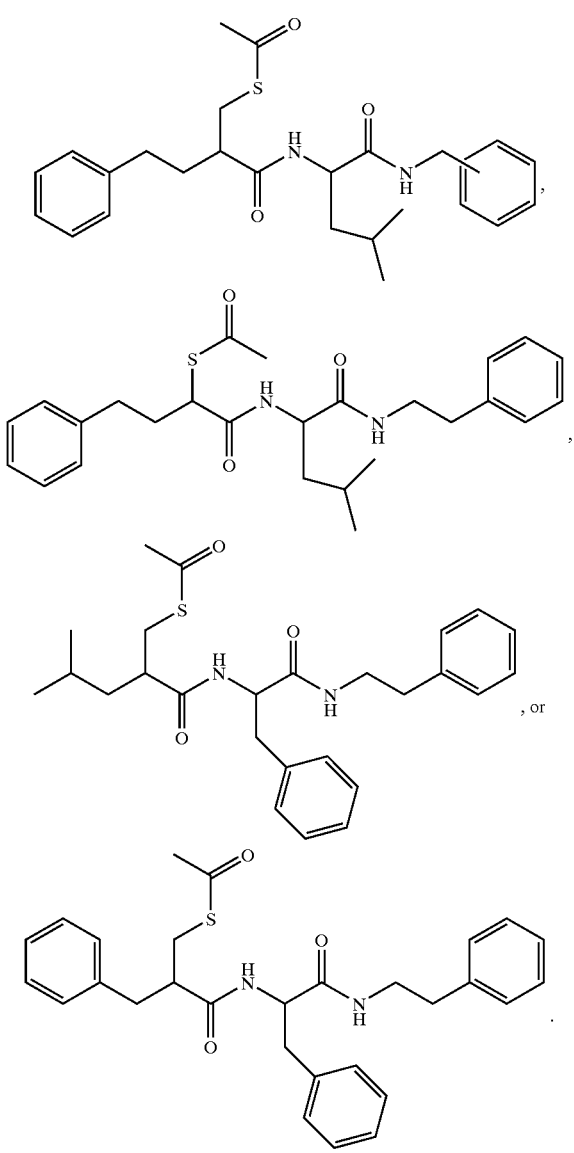

28. A method of preventing repolarization or hyperpolarization of a mammalian cell wherein the cell contains a potassium channel comprising the administration to a mammal, including a human, in need thereof, of a pharmacologically effective amount of a potassium channel blocker of structural formula I:

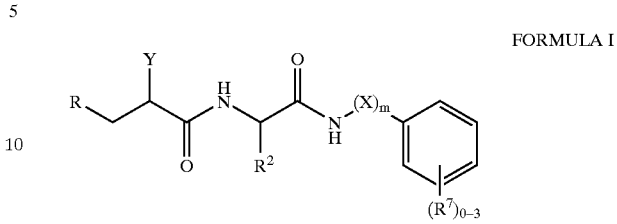

FORMULA I or a pharmaceutically acceptable salt, enantiomer, diastereomer or mixture thereof:

wherein,

R and $R^2$ independently represent $C_{1-6}$ alkyl, $(CH_2)_n$aryl, $(CH_2)_n$heteroaryl, $(CH_2)_n$heterocycloalkyl, said alkyl, aryl or heteroaryl optionally substituted with 1–3 groups of $R^3$;

Y represents —$(CH_2)_n SCOR^4$;

X represents $CH_2$, or O (in which m does not exist);

$R^3$ represents hydrogen, $C_{1-6}$ alkoxy, $C_{1-6}$ alkyl, $CF_3$, nitro, amino, cyano, $C_{1-6}$ alkylamino, or halogen and $R^4$ represents $C_{1-6}$ alkoxy, or $C_{1-6}$ alkyl;

$R^7$ represents H, halo, OH, $NO_2$, $NH_2$, CN, alkoxy, —COO—, alkoxycarbonyl, haloalkyl, alkoxycarbonylalkyl, or alkylsulphonyl;

m represents 1–3; and/or(?)

n represents 0–3.

29. A method of treating depression in a patient in need thereof comprising administering a pharmaceutically effective amount of a compound according to claim 28.

30. A method of treating cognitive disorders in a patient in need thereof comprising administering a pharmaceutically effective amount of a compound according to claim 28.

31. A method of treating arrhythmia disorders in a patient in need thereof comprising administering a pharmaceutically effective amount of a compound according to claim 28.

32. A method of treating diabetes in a patient in need thereof comprising administering a pharmaceutically effective amount of a compound according to claim 28.

* * * * *